United States Patent [19]
Dodd

[11] Patent Number: 4,677,916
[45] Date of Patent: Jul. 7, 1987

[54] WELD SCANNER GUIDE AND MAGNETICALLY SUSCEPTIBLE TRACK

[75] Inventor: Francis J. Dodd, Lafayette, Calif.

[73] Assignee: Nuclear Energy Systems, Inc., Danbury, Conn.

[21] Appl. No.: 708,173

[22] Filed: Mar. 4, 1985

[51] Int. Cl.⁴ .......................................... B61B 13/04
[52] U.S. Cl. .................................. 104/118; 238/10 R
[58] Field of Search ............. 104/118, 119; 238/10 R; 219/59.1, 60 A, 124.31, 159; 250/358.1; 228/29, 45; 24/20 CW, 20 EE, 23 EE; 285/424

[56] References Cited

U.S. PATENT DOCUMENTS

| | | | |
|---|---|---|---|
| 2,587,056 | 2/1952 | McElroy | 250/358.1 |
| 2,705,629 | 4/1955 | Miller | 104/119 |
| 3,226,027 | 12/1965 | Cable et al. | 238/1 |
| 3,380,148 | 4/1968 | Nelson et al. | 228/29 |
| 3,572,669 | 3/1971 | Brand | 104/118 |
| 3,910,480 | 10/1975 | Thatcher | 228/29 |
| 4,250,813 | 2/1981 | Slavens et al. | 228/29 |
| 4,308,648 | 1/1982 | Fay | 24/20 CW |
| 4,531,663 | 7/1985 | Kajiyama et al. | 104/118 |

Primary Examiner—Robert B. Reeves
Assistant Examiner—Dennis C. Rodgers
Attorney, Agent, or Firm—Charles J. Brown

[57] ABSTRACT

A guide and magnetically susceptible track for a weld scanner wherein a mild steel sheet metal track element is wrapped about a pipe with its end portions overlapping and the end portions are tightened together with clamp means while tabs engage notches at the opposite corners of the track element so that a guide element along the centerline of the track element is thereby self-aligned to provide a full 360° track and guide.

8 Claims, 12 Drawing Figures

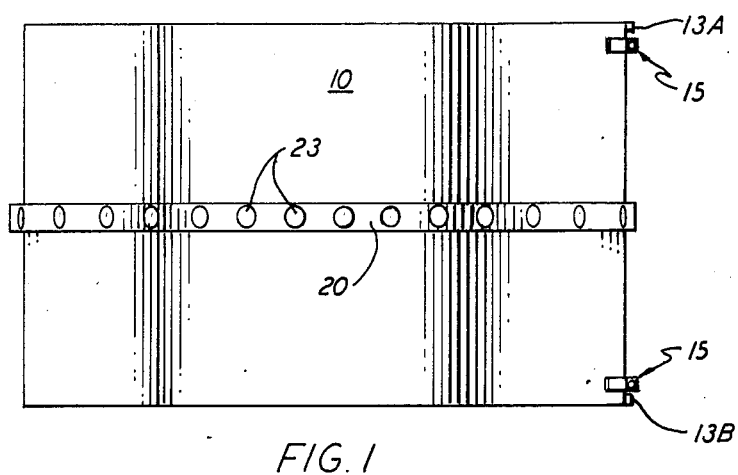
FIG. 1
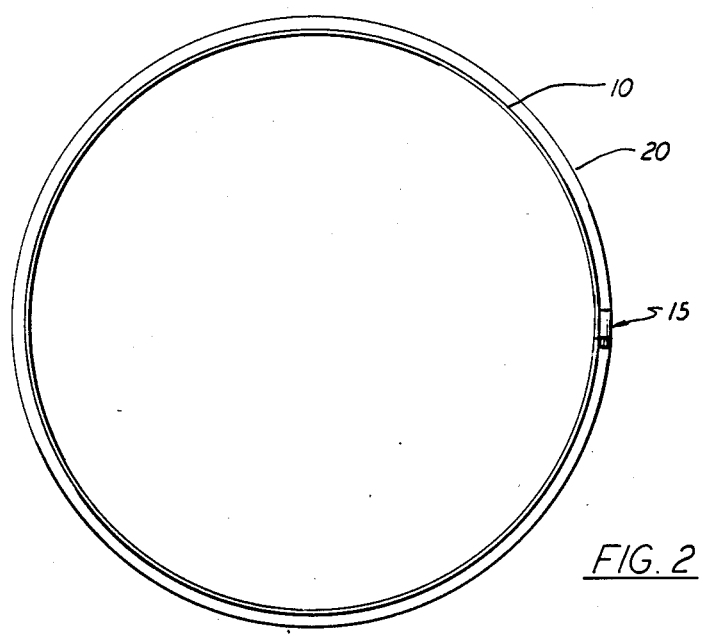
FIG. 2
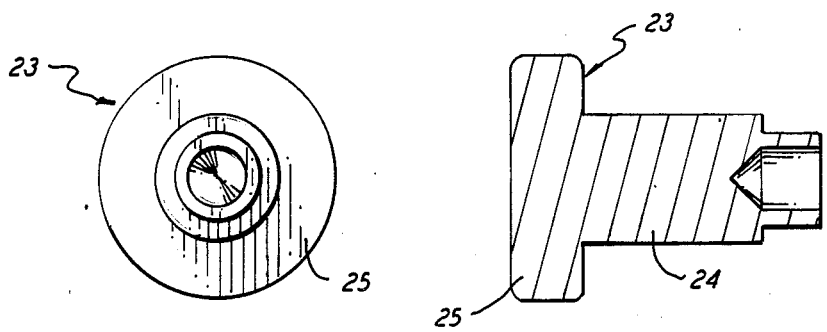
FIG. 10
FIG. 11

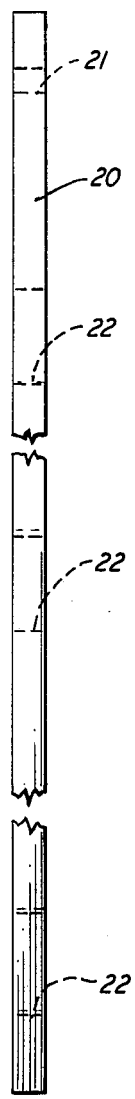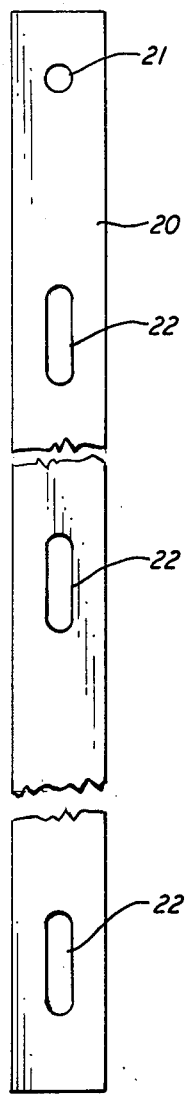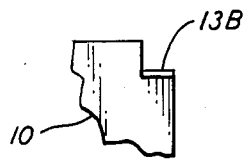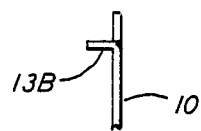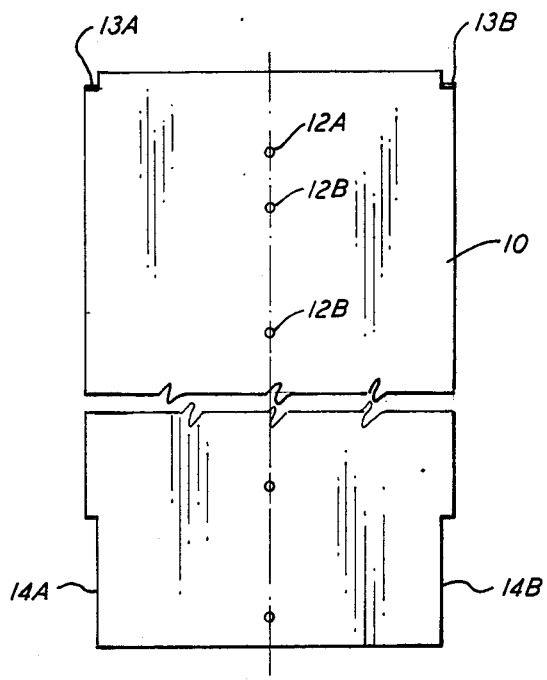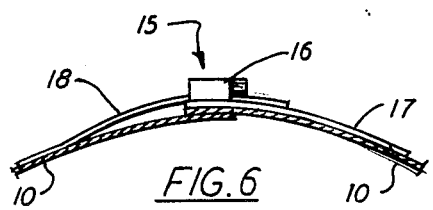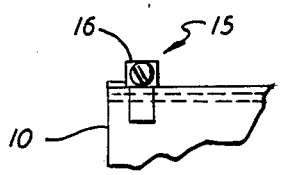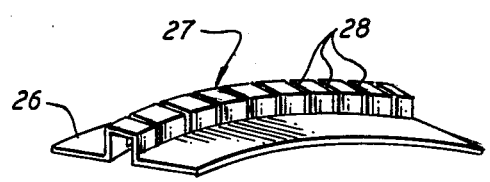

WELD SCANNER GUIDE AND MAGNETICALLY SUSCEPTIBLE TRACK

BACKGROUND OF THE INVENTION

The term "magnetic susceptibility" as used herein means the combined properties of a material which render it more or less easily magnetized, including its permeability, retentivity, coercivity, and so on. Ferromagnetic materials such as mild steel exhibit relatively high magnetic susceptibility, especially when alloyed with silicon or aluminum. Stainless steels, on the other hand, are typically of low magnetic susceptibility.

Ultrasonic pipe weld inspection is carried out, particularly in nuclear power plants, by a weld scanner device which is self-driven around the circumference of the pipe at the chosen weld and is held magnetically in place against the pipe surface regardless of the orientation of the pipe to ground. Scanners typically include a cylindrical wheel which rolls about the pipe and which has a circumferential groove of rectangular cross section. The grooved wheel rides on a flexible guide which is belted securely about the pipe. When the pipe is of stainless steel, which is often the case in nuclear power plants, a magnetically susceptible track must be associated with the flexible guide so that the scanner can hold itself magnetically in place relative to the pipe surface as it rolls around the pipe during the inspection process.

Prior art scanner tracks have been of magnetically susceptible sheet metal with nylon belts and buckles at the opposite ends thereof for attachment to a pipe. They do not permit the scanner to complete a full 360° examination of the pipe weld without repositioning the belted track at least once. Attachment of prior art belted tracks is difficult and, including repositioning time, often takes longer than the examination itself. Also the belts, buckles and associated attachment pins are essentially loose parts which could inadvertently be lost during use. Tensioning buckles used in prior art tracks are of the ratchet type adjustable only in coarse increments so that considerable force is often required to secure the assembly to the pipe. Another disadvantage has been that if the scanner reaches stops at the track ends it can fall off, and hence safety cables are necessary connecting the scanner to the track. These safety cables occasionally become entangled in the magnetic wheels of the scanner.

BRIEF STATEMENT OF THE INVENTION

The invention provides a weld scanner guide and track which is adapted to be belted about a pipe for weld inspection. The assembly includes an elongated track element of sheet metal of a length greater than the pipe circumference so that its end portions can overlap. Mating clamp means are provided at the opposite ends of the track element for tightening the track element about the pipe with one track element end portion overlapping the other track element end portion. A guide element of rectangular cross section is disposed about the circumferential centerline of the track element. The guide element is movable with respect to the track element to allow both to be bent about the pipe. The length of the guide element is such that its ends are in close proximity when the track element is tightened about the pipe.

In a preferred form the weld scanner guide and magnetically susceptible track of the invention is adapted to be belted about a pipe of low magnetic susceptibility for weld inspection. The assembly comprises an elongated flexible track element of sheet metal of relatively high magnetic susceptibility having a length greater than the pipe circumference so that its end portions can overlap. Two pairs of mating hose clamps are provided at the opposite ends of the track element on one face thereof for tightening the track element about the pipe with one track element end portion overlapping the other track element end portion. A cut-out tab is formed in each corner of that end portion of the track element adapted to underlie the other end portion and projecting normal to the aforementioned face of the track element. A notch is formed in each corner of the other end portion of the track element adapted to overlie the first-mentioned end portion and adapted to receive a corresponding tab to maintain the track element end portions in alignment as the track element is tightened about the pipe. A plastic guide element of rectangular cross section is disposed about the circumferential centerline of the track element on the aforementioned face thereof and is formed with a plurality of longitudinal slots. One end of the guide element is fixedly riveted to the track element and the remainder of the guide element is loosely riveted in said slots to the track element to allow relative movement of the guide element on the track element as both are bent about the pipe. The length of the guide element is such that its ends are aligned in close proximity to one another when the track element is fully tightened.

By this construction a full 360° track and guide is provided about the pipe so that weld examination can be done without repositioning of the scanner or the track and guide. The device is easily and quickly mounted to the pipe and is held in place by the integral hose clamps which allow infinite adjustment of the track and guide circumference. The tabs and corner notches render the track and guide self-aligning. No loose parts are present. The scanner device cannot run off the track ends and hence safety cables are unnecessary.

DESCRIPTION OF THE DRAWINGS

FIG. 1 is an elevation of the complete track and guide assembly of the invention;

FIG. 2 is an end view of the assembly of FIG. 1;

FIG. 3 is a plan view of the track element of the assembly, partly broken away, showing it in flat configuration before being belted about the pipe;

FIG. 4 is an enlarged fragmentary plan view of one tab of the track element of FIG. 3;

FIG. 5 is an enlarged fragmentary side view of the tab of FIG. 4;

FIG. 6 is an enlarged fragmentary end view of one of the pair of hose clamps of the assembly joining the opposite end portions of the track;

FIG. 7 is an enlarged fragmentary side view of the hose clamp of FIG. 6;

FIG. 8 is a plan view, partly broken away, of the guide element assembly in flat configuration before being belted about the pipe;

FIG. 9 is a side view of the guide element of FIG. 8;

FIG. 10 is an end view of the one of the rivets for connecting the guide to the track;

FIG. 11 is a longitudinal cross section of the rivet of FIG. 10; and

FIG. 12 is a fragmentary perspective view of an alternative form of one-piece track and guide illustrated in curved configuration as when belted on a pipe.

DESCRIPTION OF PREFERRED EMBODIMENT

Referring first to FIGS. 1 and 3, the assembly of the invention includes an elongated flexible track element 10 of sheet metal having a relatively high magnetic susceptibility. It may be of mild steel of eighteen gauge thickness. Approximately six inches is an appropriate width dimension and its length varies with the diameter of the pipe to which it is to be applied. When so applied the ends of the track element 10 should overlap as shown in FIG. 6 and hence for a pipe of ten inches diameter the overall length of the track element 10 would be 34.68 inches. Referring to FIG. 3 below a hole 12A is formed on the longitudinal centerline of the track element 10 approximately one and one-quarter inch from one end thereof and a series of holes 12B are also formed along the centerline spaced approximately two inches apart with the first of the series and approximately one inch from the hole 12A.

Referring to FIGS. 3 and 5, cut-out 13A and 13B are formed in opposite corners of one end portion of the track element and they project normally from one face thereof. One cut-out tab 13B is shown enlarged in FIGS. 4 and 5. Each of the tabs 13A and 13B may be one-tenth of an inch square.

Notches 14A and 14B are formed in opposite corners of the other end portion of the track element 10 as shown particularly in FIG. 3. Each of the notches 14A and 14B may have a length parallel to the longitudinal axis of the track 10 of approximately two and one-quarter inches so that the tabs 13A and 13B do not reach the ends of the notches when the track element is tightened about the pipe. The width of each notch may be one-eighth of an inch so that the sides of the tabs 13A and 13B engage the sides of the notches and hold the overlapping end portions of the track element in correct alignment. Referring to FIGS. 6 and 7, two pairs of mating hose clamp assemblies 15 are provided. A hose clamp assembly includes a barrel 16 and an associated strap 17 at one end of the track element 10 and an associated slotted strap 18 at the other end of the track element 10. These hose clamps are conventional in design and are readily available shelf items. A threaded screw is located within the barrel 16 and as it is turned it engages cross slots on the strap 18 to either draw the ends of the track element toward one another in overlapped relation or apart for purposes of separating them. Each hose clamp assembly 15 with its respective straps and barrel is located on that face of the track element from the which tab stops 13A and 13B project. The straps 17 and 18 of the hose clamp assemblies are spot welded to the track element 10.

Referring now to FIGS. 8 and 9 a plastic guide element 20 is illustrated. It may be of a polycarbonate material. The guide element 20 is of rectangular cross section and for use with a pipe ten inches in diameter it should have a length of 33.68 inches so that its ends are in close proximity but not abutting when the track element is tightened about the pipe. Its width may be approximately four-tenths of an inch and its thickness may be 0.156 inch. A one-eighth inch hole 21 is drilled at one end portion of the guide element 20 and longitudinal slots 22 are spaced every two inches apart along the length of the guide. Each slot 22 may have a width of one-eight of an inch and a length of approximately one-half inch.

The guide element 20 is fixedly riveted to the track element 10 by one of the types of rivets 23 shown in FIGS. 10 and 11 at the hole 21 at one end of the track 10. The remainder of the length of the guide is loosely held by the rivets 23 in the holes 12B in the track element and the slots 22 in the guide element. Each rivet 23 has a shank 24 slightly smaller in diameter than the slot width and a head 25 which is larger than the slot width. This allows relative movement of the guide 20 on the track element 10 as both are bent about the pipe. As noted above the length of the guide is such that its ends are in close proximity when the track element is tightened and they are aligned because of the interaction of the tabs 13A and 13B with the sides of the notches 14A and 14B.

It will be apparent that the assembly of the invention includes no loose parts. In use it is wrapped manually around the pipe in question adjacent the weld to be inspected and the straps 18 of the hose clamps 15 are inserted through the screw barrels 16. In this position the tab stops 13A and 13B are located in the slots 14A and 14B. The screws of the hose clamps are turned so that the straps 18 are drawn into the barrels 16 and the opposite end portions of the track element 10 overlapping one another are drawn further together as well. When the tabs 13A and 13B acting in the notches 14A and 14B align the opposite ends of the guide element 20. This provides a continuous 360 degrees guide for the drive wheel of the scanner so that the scanner cannot run off the guide element and no attachment cable is necessary. The track element 10 of magnetically susceptible metal provides the surface to which the scanner adheres as it travels about the pipe during the inspection process.

Turning now to FIG. 12 an alternate form of the assembly of the invention is shown which does not involve a guide element 20 separate from the track element 10. In the FIG. 12 embodiment a sheet metal track element 26 is stamped to form a central longitudinal rib 27 along its centerline. The rib 27 is upstanding and is of rectangular cross section of a shape suitable to be engaged by the slotted drive wheel of the scanner device. A plurality of slits 28 are formed laterally in the rib 27 throughout the length thereof to allow it to flex when the track element 26 is wrapped about a pipe. The slits 28 also permit meshing engagement with a scanner drive gear if desired. It will be seen that the neutral bending axis of the track element 26 of FIG. 12, which is to say that axis which does not change length when the element 24 is bent in a circle, is along the inside face of the track element 26 engaging the pipe. The slits 28 open at their outer ends in the process of bending. As in the prior embodiment wherein the guide element 20 is not as long as the track element 10, the rib 27 stops short of the end of the track element 26 so that the ends of the track element can overlap when belted about a pipe, though this does not appear in the fragmentary section of the ribbed guide shown in FIG. 12.

The scope of the present invention is to be taken from the following claims rather than the foregoing description of preferred embodiment.

I claim:

1. A weld scanner guide and magnetically susceptible track adapted to be belted about a pipe for weld inspection comprising (a) an elongated flexible track element of sheet metal of a length greater than the pipe circumference so that its end portions can overlap, (b) mating clamps means at the opposite ends of the track element thereof for tightening the track element about the pipe with one track element end portion overlapping the other track element end portion, (c) a guide element of rectangular cross section disposed about the circumferential centerline of the track element and whether said track is bent about the pipe or in an unbent state said guide element is fixed against overall longitudinal movement relative thereto, (d) the guide element being otherwise longitudinally movable with respect to the track element to allow both to be bent about the pipe, and (e) the length of the guide element being such that its ends are in close proximity to one another when the track element is tightened about the pipe.

2. A guide and track according to claim 1 wherein the guide element is fixed to the track element at one end and the remainder of the guide element is loosely secured to the track element to allow relative movement of the guide element on the track element as both are bent about the pipe.

3. A guide and track according to claim 1 wherein the guide element is an integral rib element formed in the track element and having lateral slits to permit bending with the track element.

4. A weld scanner guide and track adapted to be belted about a pipe for weld inspection comprising
(a) an elongated flexible track element of sheet metal of a length greater than the pipe circumference so that its end portions can overlap,
(b) mating clamp means at the opposite ends of the track element for tightening the track element about the pipe with one track element end portion overlapping the other track element end portion,
(c) a pair of tabs formed in that end portion of the track element adapted to underlie the other end portion and projecting normal to the aforementioned face of the track element,
(d) a pair of notches formed in the other end portion of the track element adapted to overlie the other end portion and adapted to receive the tabs to align the ends of the track element as it is tightened about the pipe.
(e) a guide element of rectangular cross section disposed about the circumferential centerline of the track element and whether said track is bent about the pipe or in an unbent state said guide element is fixed against overall longitudinal movement relative thereto,
(f) the guide element being otherwise longitudinally movable with respect to the track element to allow both to be bent about the pipe, and
(g) the length of the guide element being such that its ends are in close proximity to one another when the track element is tightened about the pipe.

5. A guide and track according to claim 4 wherein the guide element is fixed to the track element at one end and the remainder of the guide element is loosely secured to the track element to allow relative movement of the guide element on the track element as both are bent about the pipe.

6. A guide and track assembly according to claim 5 wherein the mating clamp means comprises two pairs of hose clamps.

7. A guide and track according to claim 4 wherein the guide element is an integral rib element formed in the track element and having lateral slits to permit bending with the track element.

8. A weld scanner guide and magnetically susceptible track adapted to be belted about a pipe of low magnetic susceptibility for weld inspection comprising
(a) an elongated flexible track element of sheet metal of relatively high magnetic susceptibility of a length greater than the pipe circumference so that its end portions can overlap,
(b) mating clamp means at the opposite ends of the track element on one face thereof for tightening the track element about the pipe with one track element end portion overlapping the other track element end portion,
(c) a cut-out tab formed in each corner of that end portion of the track element adapted to underlie the other end portion and projecting normal to the aforementioned face of the track element,
(d) a notch formed in each corner of the other end portion of the track element adapted to overlie the other end portion and adapted to receive the corresponding tab to align the ends of the track element as the track element is tightened about the pipe.
(e) a plastic guide element of rectangular cross section disposed about the circumferential centerline of the track element on the aforementioned face thereof and formed with a plurality of longitudinal slots,
(f) one end of the guide element being fixedly riveted to the track element and the remainder of the guide element being loosely riveted in said slots to the track element to allow relative movement of the guide on the track as both are bent about the pipe, and
(g) the length of the guide element being such that its ends are in close proximity to one another and aligned when the track element is tightened about the pipe.

* * * * *